United States Patent [19]
Glenn, Jr. et al.

[11] Patent Number: 5,885,948
[45] Date of Patent: *Mar. 23, 1999

[54] CRYSTALLINE HYDROXY WAXES AS OIL IN WATER STABILIZERS FOR SKIN CLEANSING LIQUID COMPOSITION

[75] Inventors: Robert Wayne Glenn, Jr., Maineville, Ohio; James Charles Dunbar, Weybridge, England; Mark Leslie Kacher, Mason, Ohio; Fernando Ray Tolléns, Cincinnati, Ohio; Raymond Edward Bolich, Jr., Maineville, Ohio; Robert Raymond Schmidt, Wright, Ky.; David John Weisgerber, Cincinnati; Wayne Ellis Eccard, Cleves, both of Ohio

[73] Assignee: The Procter & Gamble Company, Cincinnati, Ohio

[*] Notice: The term of this patent shall not extend beyond the expiration date of Pat. No. 5,716,920.

[21] Appl. No.: 959,969

[22] Filed: Oct. 24, 1997

Related U.S. Application Data

[63] Continuation of Ser. No. 529,258, Sep. 15, 1995, abandoned, and a continuation-in-part of Ser. No. 388,961, Feb. 15, 1995, abandoned.

[51] Int. Cl.$^6$ ............................... C11D 3/20; A61K 7/50
[52] U.S. Cl. ..................... 510/130; 510/137; 510/138; 510/159; 510/417; 510/427; 510/428; 510/437; 424/401
[58] Field of Search .................................. 510/130, 137, 510/138, 159, 417, 427, 428, 437; 424/401

[56] References Cited

U.S. PATENT DOCUMENTS

| | | | |
|---|---|---|---|
| 3,242,092 | 3/1966 | Bechtold | 252/138 |
| 3,829,563 | 8/1974 | Barry et al. | 424/70 |
| 4,119,712 | 10/1978 | Goldner et al. | 424/63 |
| 4,457,916 | 7/1984 | Hayashi et al. | 424/101 |
| 4,478,853 | 10/1984 | Chaussee | 424/358 |
| 4,820,508 | 4/1989 | Wortzman | 424/59 |
| 4,837,005 | 6/1989 | Brode, II et al. | 424/47 |
| 4,844,891 | 7/1989 | Rosen et al. | 424/76.4 |
| 4,853,222 | 8/1989 | Avalle | 424/195.1 |
| 4,992,477 | 2/1991 | Geria | 514/782 |
| 5,002,974 | 3/1991 | Geria | 514/782 |
| 5,006,337 | 4/1991 | Motitschke et al. | 424/195.1 |
| 5,024,831 | 6/1991 | Kurisaki et al. | 424/69 |
| 5,059,414 | 10/1991 | Dallal et al. | 424/70 |
| 5,135,748 | 8/1992 | Ziegler et al. | 424/401 |
| 5,144,744 | 9/1992 | Campagnoli | 29/446 |
| 5,160,738 | 11/1992 | Macaulay et al. | 424/401 |
| 5,221,530 | 6/1993 | Janchitraponvej et al. | 424/70 |
| 5,260,051 | 11/1993 | Cho | 424/57 |
| 5,308,526 | 5/1994 | Dias et al. | 252/125 |
| 5,312,555 | 5/1994 | Kacher et al. | 252/125 |
| 5,352,387 | 10/1994 | Rahman et al. | 252/548 |
| 5,534,265 | 7/1996 | Fowler et al. | 424/489 |
| 5,585,104 | 12/1996 | Ha et al. | 424/401 |
| 5,674,511 | 10/1997 | Kacher et al. | 424/401 |
| 5,716,920 | 2/1998 | Glenn, Jr. et al. | 510/159 |

FOREIGN PATENT DOCUMENTS

| | | | |
|---|---|---|---|
| 3836907 A1 | 5/1990 | Germany | A61K 7/075 |
| 56-62899 | 5/1981 | Japan | C11D 3/48 |
| 63-126541 | 5/1988 | Japan | B01J 13/00 |
| 68/0771 | 9/1969 | South Africa . | |
| 1801475 A1 | 3/1993 | U.S.S.R. | A61K 7/00 |
| WO92/07547 | 5/1992 | WIPO | A61K 7/16 |
| WO94/15580 | 7/1994 | WIPO | A61K 7/42 |
| WO94/18277 | 8/1994 | WIPO | C09C 1/30 |

OTHER PUBLICATIONS

CAB–O–SIL® Fumed Silica in Cosmetic and Personal Care Products, Cabot Corporation, Mar. 1992.
Microfine Bentonite, American Colloid Company, Industrial Chemical Marketing Group, IL. date unknown.

*Primary Examiner*—Lorna Douyon
*Attorney, Agent, or Firm*—Darryl C. Little; Tara M. Rosnell; George W. Allen

[57] ABSTRACT

A stress stable lathering skin cleansing liquid composition comprising by weight parts of the liquid composition:
(a) from about 0.5 parts to 10 parts of a crystalline, hydroxy-containing stabilizer; for example trihydroxystearin;
(b) from about 1 part to about 30 parts of lipid skin moisturizing agent;
(c) from about 5 parts to about 30 parts of surfactant having a combined CMC equilibrium surface tension value of from 15 to 50;
(d) water;
wherein said stress stable lathering skin cleansing liquid composition has a Lipid Deposition Value (LDV) of from about 5 to about 100 and wherein the composition is stable for at least two weeks at 100° F.

19 Claims, No Drawings

CRYSTALLINE HYDROXY WAXES AS OIL IN WATER STABILIZERS FOR SKIN CLEANSING LIQUID COMPOSITION

This is a continuation of application Ser. No. 08/529,258, filed on Sep. 15, 1995 now abandoned, and is a continuation-in-part of application Ser. No. 08/388,961, filed on Feb. 15, 1995 now abandoned.

TECHNICAL FIELD

The present invention relates to personal skin moisturizing and cleansing compositions.

BACKGROUND OF THE INVENTION

Moisturizers are usually applied directly to the skin as leave-on products. Personal cleansing products are usually applied with water as a foam or lather and rinsed off with clear water. Ideal rinse off personal cleansers should cleanse the skin gently, causing little or no irritation without defatting and or drying the skin and without leaving skin taut after frequent use. Most lathering personal cleansing products, bar soaps, liquids and syndet liquids fail in this respect.

Some current commercial personal cleansing liquids claim to "moisturize" the skin. But, most of these current cleansing liquid products do not deliver an adequate moisturizing benefit. Therefore, users typically must moisturize their skin with a separate leave-on product following cleansing.

It would be highly desirable to improve the delivery of skin moisturizers from a cleansing liquid composition over the current commercial personal cleansing liquids. If this were accomplished it would provide users with the convenience of obtaining both a cleansing and a moisturizing benefit from a single product.

Dual cleansing and lipid moisturizing liquid compositions are very difficult to formulate and process. One reason is the cleansing ingredients, in general, tend to be incompatible with the lipid moisturizing ingredients. Another problem is processing on a commercial scale. Yet another problem is getting the lipid in the liquid to deposit on the skin of the user. The deposition of lipid moisturizer from the liquid, onto the skin can be very low due to loss of the lipid in the wash and the rinse. Conversely, it can feel too sticky if deposited on the skin. Still another problem is formulating a dual liquid that lathers well. Another problem is formulating a dual liquid that is storage stabile. Yet another problem is formulating a dual liquid that is stress stable.

The actual deposition of lipid moisturizer from a lathering dual liquid composition is essential for effective lipid benefit. No known commercial prior art liquid that claims to be a cleansing and lipid moisturizing liquid, deposits as much 3 micrograms of lipid moisturizer per cm. sq. of washed skin.

U.S. Pat. No. 3,829,563, Barry et al., issued Aug. 13, 1974, discloses an emollient cleansing liquid and paste composition containing 10–70 parts by weight petrolatum with up to 98 parts, preferably, 95–98 parts, having a diameter particle size smaller than 5 microns.

U.S. Pat. No. 5,308,526, Dias et. al., issued May 3, 1994, incorporated herein by reference, discloses liquid skin compositions with up to 5 parts petrolatum wherein 20–80 parts of said petrolatum particles have a particle size from 10–120 microns.

U.S. Pat. No. 5,312,559, Kacher et al., issued May 17, 1994, incorporated herein by reference, discloses semi-solid compositions of 60,000 to 400,00 cps containing 0.5 parts to 15 parts petrolatum having a particle size distribution in which 20% to 80% of the particles are 10–120 microns.

Shelf stable dual skin cleansing liquid composition, as defined herein, are stable for at least two weeks at room temperature. However, such composition are not required to be stable under stress conditions, as defined below herein.

Therefore, it is an object of the present invention to provide an effective, yet gentle, dual skin cleansing liquid composition which is stress stable.

It is an object of the present invention to provide an effective, yet gentle, dual skin cleansing liquid composition which actually deposit enough lipid on the skin to provide superior skin moisturizing and sensory benefits while maintaining its lathering and cleaning properties.

SUMMARY OF THE INVENTION

The present invention relates to a stress stable lathering skin cleansing liquid composition comprising by weight parts of the liquid composition:

(a) from about 0.5 parts to 10 parts of a crystalline hydroxyl-containing stabilizer selected from the group consisting of:

(i)

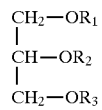

wherein
$R_1$ is —

$R_2$ is $R_1$ or H
$R_3$ is $R_1$ or H
$R_4$ is $C_{0-20}$ Alkyl
$R_5$ is $C_{0-20}$ Alkyl, or H
$R_6$ is $C_{0-20}$ Alkyl or H
$R_4 + R_5 + R_6 = C_{10-22}$
and wherein $1 \leq x+y \leq 4$;

(ii)

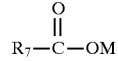

wherein
$R_7$ is —$R_4(CHOH)_xR_5(CHOH)_yR_6$
M is Na+, K+ or Mg++, or H; and
iii) mixtures thereof;

(b) from about 1 part to about 30 parts of lipid skin moisturizing agent; wherein said lipid has a shear index (n) at 35° C. in the range 0.1 to 0.9 and a consistency k at 35° C. in the range 10 to 5,000 poise;

(c) from about 5 parts to about 30 parts of surfactant, wherein said surfactant has a combined CMC equilibrium surface tension value of from 15 to 50; and (d) water;

wherein said stress stable lathering skin cleansing liquid composition has a Lipid Deposition Value (LDV) of from about 5 to about 1000 and wherein said composition is stable for at least two weeks at 100° F. (38° C.).

DETAILED DESCRIPTION OF THE INVENTION

The present invention can provide a dual cleansing and lipid moisturizing liquid composition: 1) which produces an abundant, stable, high quality lather, 2) which is an effective skin cleanser, 3) which is very mild to the skin and ocular mucosae, 4) which actually delivers an effective amount of a lipid moisturizing agent to the skin of the user during the wash; 5) which is non-sticky after use, and 6) which is stress stable.

The present liquid is a stress stable lathering skin cleansing liquid composition comprising by weight parts of the following liquid composition:

(a) from about 0.5 parts to 10 parts of a crystalline hydroxy-containing stabilizer selected from the group consisting of:

(i)

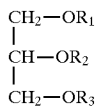

wherein
R$_1$ is —

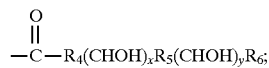

R$_2$ is R$_1$ or H
R$_3$ is R$_1$ or H
R$_4$ is C$_{0-20}$Alkyl
R$_5$ is C$_{0-20}$Alkyl, or H
R$_6$ is C$_{0-20}$Alkyl or H
R$_4$+R$_5$+R$_6$=C$_{10-22}$
and wherein 1<x+y<4;

(ii)

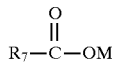

wherein
R$_7$ is —R$_4$(CHOH)$_x$R$_5$(CHOH)$_y$R$_6$
M is Na+, K+ or Mg++, or H; and iii) mixtures thereof;

(b) from about 1 part to about 30 parts of lipid skin moisturizing agent; wherein said lipid has a shear index at 35° C. in the range 0.1 to 0.9 and a consistency k at 35° C. in the range 10 to 5,000 poise;

(c) from about 5 part to about 30 parts of surfactant, wherein said surfactant has a combined CMC equilibrium surface tension value of from 15 to 50; and (d) water;

wherein said stress stable lathering skin cleansing liquid composition has a Lipid Deposition Value (LDV) of from about 5 to about 1000 and wherein said composition is stable for at least two weeks at 100° F. (38° C.).

GLOSSARY OF TERMS

The term "Shelf Stable Liquid Cleanser," as used herein, is defined as a neat lathering skin cleansing liquid composition that under ambient conditions does not phase separate for at least two weeks, preferably for at least six months, and more preferable never.

The term "Stress Stable Liquid Cleanser," as used herein, is defined as a neat lathering skin cleansing liquid composition that under 100° F. (38° C.) condition does not phase separate for at least two weeks, preferably for at least six months, and more preferable never.

The term "Pseudoplastic" as used herein refers to fluids which show a marked decrease in viscosity as shear rate increases. This behavior is also referred to as shear thinning, which means that the resistance of the material to flow decreases as the energy required to sustain flow at high shear is reduced.

The term "Thixotropy" as used herein is defined as the ability of the system to exhibit lower viscosites as a function of shearing and its ability to have its structure reformed over a period of time after the shear is removed.

The term "Crystalline waxes", as used herein, refers to solid water insoluble particulates of a wax or waxy substance dispersed in the liquid cleanser. Crystalline waxes are formed via solubilization in the continuous phase of liquid composition (above melting point of the wax) followed by rapid cooling.

The term "Water Dispersible Gel Forming Polymer" as used herein means that the polymer is water dispersible and forms a gel in water of the liquid cleanser at 5° to 40° C.

Vaughan Solubility Parameter (VSP) is a calculated parameter used to define a lipid's solubility. Vaughan parameters typically have a range of 5–25.

Lipid Deposition Value (LDV) is a measure of how much lip skin from compositions herein, the reading corresponds to the amount measured using a Sebumeter (typically the mean of three readings), as defined in Lipid Deposition Protocol herein.

Equilibrium Surface Tension is a measure of surface tension of a surfactant as measured at the critical micelle concentration at 25° C.; units are dynes/cm.

Consistency, k, is a measure of viscosity, used in combination with Shear index, to define viscosity for materials whose viscosity is a function of shear. The measurements are made at 35° C. and the units are poise (equal to 100 cps).

Shear index, n, is a measure of viscosity, used in combination with Consistency, to define viscosity for materials whose viscosity is a function of shear. The measurements are made at 35° C. and the units are dimensionless.

All parts, percentages and ratios used herein are by weight basis and all measurements are at 25° C., unless otherwise indicated.

The dual cleansing and lipid moisturizing liquid compositions of the present invention are oil-in-water emulsions. The lipid and aqueous phases of these emulsions, as well as the emulsions themselves and the preparation thereof, are described in detail as follows.

A. The Aqueous Phase

The aqueous phase of the oil-in-water emulsions of the present invention comprises a crystalline, hydroxy-containing stabilizer, a surfactant, and water, along with various optional ingredients. Each of the components of the aqueous phase of the emulsions herein is described in detail as follows.

1. THE CRYSTALLINE, HYDROXYL-CONTAINING STABILIZER

A crystalline, hydroxyl-containing stabilizer is included in the aqueous phase of the emulsions of the present invention. This stabilizer can be a hydroxyl-containing fatty acid, fatty ester or fatty soap water-insoluble wax-like substance or the like. The stabilizer is used to form a crystalline stabilizing network in the emulsion that prevents the lipid droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the oil-in-water emulsion to separate upon lathering, and thereby provide for increased lipid deposition onto the skin. This is particularly true when the oil-in-water cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

The crystalline, hydroxyl-containing stabilizer comprises from about 0.5 parts to 10 parts, preferably from 0.75 to 8 parts, more preferably from 1.25 parts to about 5 parts of the liquid cleansing emulsion compositions herein. The said stabilizer is insoluble in water under ambient to near ambient conditions.

The stabilizer is selected from the group consisting of:

(i)

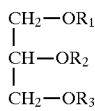

wherein
$R_1$ is —

$R_2$ is $R_1$ or H
$R_3$ is $R_1$ or H
$R_4$ is $C_{0-20}$ Alkyl
$R_5$ is $C_{0-20}$ Alkyl, or H
$R_6$ is $C_{0-20}$ Alkyl or H
$R_4+R_5+R_6=C_{10-22}$
and wherein $1 \leq x+y \leq 4$;

(ii)

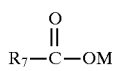

wherein
$R_7$ is —$R_4(CHOH)_xR_5(CHOH)_yR_6$
M is Na+, K+ or Mg++, or H; and
iii) mixtures thereof, Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the emulsion compositions herein.

2. THE LATHERING SURFACTANT

The aqueous phase of the liquid cleansing emulsion compositions of the present invention also comprises a lathering surfactant selected from the group consisting of anionic surfactants; nonionic surfactants, cationic surfactants, amphoteric surfactants, and mixtures thereof.

The lathering surfactant is defined herein as a surfactant or surfactant mixture thereof that when combined have an equilibrium surface tension of between 15 and 50 dynes/cm, more preferably between 25 and 40 dynes/cm as measured at the CMC (critical micelle concentration) at 25° C. Some surfactant mixes can have a surface tension lower than those of its individual components.

The personal cleansing and moisturizing liquid emulsion compositions herein comprise from about 5 part to about 30 parts, preferably from about 5 parts to about 25 parts, and most preferably from about 10 parts to about 25 parts of a lathering surfactant.

Anionic surfactants useful herein include: acyl isethionates, acyl sarcosinates, alkylglycerylether sulfonates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphates, the alkyl ether sulfates (with 1 to 12 ethoxy groups) and mixtures thereof, wherein said surfactants contain C8 to C22 alkyl chains and wherein the counterion is selected from the group consisting of: Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8 to about 20 parts.

Amphoteric synthetic surfactants cannot serve as the sole surfactant in this product, but are preferred as a co-surfactant at a lower level of from about 1 part to about 10 parts, by weight and the more preferred types are selected from alkyl-ampho mono- and di-acetates, alkyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1 parts to about 15 parts by weight. The more preferred types selected from the group consisting: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers such as polyoxamines and poloxamers, sorbitan esters and alcohol esters, and mixtures thereof.

In a preferred embodiment of the present invention, the liquid emulsions compositions herein contain from 0.5 parts to 8 parts C8–14 soap; where the soap has a counterion selected from the group consisting of K and $N(CH2CH20OH)_3$, and mixtures thereof, in addition to the lathering synthetic surfactant.

Cationic synthetic surfactant cannot serve as the sole surfactant in this product, but are preferred as a co-surfactant at a lower level of from about 0.5 parts to about 6 parts, by weight. The more preferred types of cationic surfactants are selected from the group consisting: alkyl trimonium chloride and methosulfate, and dialkyldimonium chloride and methyl sulphate, and alkyl alkonium chloride and methyl sulphate and mixtures thereof. These surfactants contain C 12 to C24 carbon atoms per alkyl chain. The most preferred cationic is selected from the group consisting of stearalkonium chloride, stearyltrimonium chloride, Di-stearyl-dimonium chloride, and mixtures thereof. Cationic surfactants may also act as a lipid deposition aid.

3. WATER

The moisturizing and cleansing liquid emulsion compositions of the present invention comprise water as an essential component. The water is typically present at a level of from about 30 parts to about 80 parts, preferably from about 40 parts to about 75 parts, and most preferably from about 40 to about 65 parts of the liquid cleansing emulsions of the present invention.

4. OPTIONAL INGREDIENTS

The water phase of the oil-in-water emulsions of the present invention can also contain a number of optional ingredients in addition to the crystalline, hydroxyl-containing stabilizer, surfactant and water.

For example, the liquid cleansing emulsions of the present invention can optionally include water-dispersible, gel-forming polymers in the aqueous phase of the emulsion. This polymer is preferably a anionic, nonionic, cationic or hydrophobically modified polymer, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and non-ionic cellulose resins; cationic copolymers of dimethyl-dialkylammonium chloride and acrylic acid; cationic homopolymers of dimethyldialkylammonium chloride; cat-ionic polyalkylene and ethoxypolyalkylene imines polyeth-ylene glycol of molecular weight from 100,000 to 4,000,000; and mixtures thereof. Preferably, the polymer is selected form the group consisting of Sodium Polyacrylate, Hydroxy Ethyl Cellulose, Cetyl Hydroxy Ethyl Cellulose, and Polyquaternium 10.

The polymer is preferably included in the emulsions of the present invention at a level of from about 0.1 parts to 1 part, more preferably 0.1 parts to 0.5 parts. The polymers can improve the sensory feel of the lipid on skin in addition to providing product stabilization. The improved sensory feel results from reduced tackiness and greasiness and improved smoothness. It is an especially preferred embodi-ment to use mixture of polymers, some of which are preferred for product stabilization, some are preferred for improved sensory feel. Preferred polymers to improve sen-sory feel are selected from the group consisting: of poly-ethylene glycol, hydroxypropyl guar, guar hydroxypropylt-rimonium chloride, polyquaternary 3, 5, 6, 7, 10, 11 and 24 and mixtures thereof.

Another highly preferred optional component of the present compositions are one or more humectants and sol-utes. A variety of humectants and solutes can be employed and can be present at a level of from about 0.5% to about 25%, more preferably from about 3.0% to about 20%. The humectants and solutes are non-volatile, organic materials having a solubility of a least 5 parts in 10 parts water. A preferred water soluble, organic material is selected from the group consisting of a polyol of the structure:

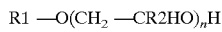

where R1=H, C1–C4 alkyl; R2=H, CH$_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L- forms); pyrrolidone car-boxylic acid; hyaluronic acid; lactamide monoethanolamine; acetamide monoethanolamine; urea; and ethanol amines of the general structure (HOCH$_2$CH$_2$)$_x$NH$_y$ where x=1–3; y=0–2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Preferred water soluble organic material are selected from the group consisting of glycerine, polyoxypropylene (1) glycerol and polyoxypropylene (3) glycerol, sorbitol, buty-lene glycol, propylene glycol, sucrose, and urea and trietha-nolamine.

The use of oil thickening polymers, such as those listed in EP 0 547 897 A2 to Hewitt, published 23/06/93, incorpo-rated herein by reference, can also be included in the water phase of the emulsions of the present invention.

A variety of additional ingredients can be incorporated into the compositions of the present invention. These mate-rials including, but not limited to, liquid appearance aids, salts and their hydrates and other "filler materials" are listed in U.S. Pat. No. 5,340,492, to Kacher et al., issued Aug. 23, 1994, and U.S. Pat. No. 4,919934, to Deckner et al., issued Apr. 24, 1990; which is incorporated herein by reference.

Other non limiting examples of these additional ingredi-ents include vitamins and derivatives thereof (e.g., ascorbic acid, vitamin E, tocopheryl acetate, and the like); sun-screens; thickening agents (e.g., polyol alkoxy ester, avail-able as Crothix from Croda at levels up to 2% and xanthan gum at levels up to about 2%); preservatives for maintaining the anti microbial integrity of the compositions; anti-acne medicaments (resorcinol, salicylic acid, and the like); anti-oxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), additives to impart a draggy rinse feel (e.g., fumed silica at levels from about 0.5 parts to about 5 parts), additives to enhance deposition (e.g., maleated soybean oil at levels up to 3% or from about 0.5 to about 3 parts), lakes, colorings, and the like (e.g., clove oil, menthol, camphor, eucalyptus oil, and eugenol).

B. The Lipid Phase

The oil-in-water emulsions of the present invention also contain a lipid phase which comprises from about 1 parts to about 30 parts, preferably from about 5 parts to about 30 parts, more preferably from about 10 to about 25 parts of a lipid skin moisturizing agent. The lipid skin moisturizing agent provides the skin of the user with a moisturization benefit via deposition of the lipid on skin during use. In this invention the lipid skin moisturizing agent is defined with scrutiny. The lipid type and its physical properties in this present invention hold the key to the overall product effectiveness, and is restricted to a hydrophobic material with the following rheological properties.

Two types of rheological parameters are used to define the lipid used herein. The viscosity of the fluid is represented by consistency (k) and shear index (n). While not being bound by any theory, lipids outside of the rheology properties defined herein below are either too easily emulsified and hence will not deposit, or are too "stiff" to adhere or deposit on to skin and provide a moisturization benefit. In addition, the rheological properties of the lipid are also important to user perception. Some lipids, on deposition to the skin, are considered too sticky and are not preferred by the user.

Lipid Rheological Table 1

| Range | k<br>poise (l/sec)n − 1 | n<br>(dimensionless) |
|---|---|---|
| Most preferred | 50–2,000 | 0.20–5 |
| More Preferred | 10–3,000 | 0.1–0.5 |
| Preferred | 5–5000 | 0.1–0.9 |

As shown in the Lipid Rheological Table above, suitable lipids for use herein have a shear index, n, of from about 0.1 to about 0.9, preferably from about 0.1 to about 0.5, more preferably from about 0.2 to about 0.5, and a consistency, k, of: from 5 to 5,000 poise; preferably 10 to 3000 poise; more preferably 50 to 2,000 poise at 35° C. The rheology of some preferred lipids is set forth in the following table:

Lipid Rheological Table 2

| Lipids | Consistency, k | shear index |
|---|---|---|
| Units | poise | n |
| Water | 0.01 | 1.0 |
| Microcrystalline Wax (MC) | ** | ** |
| 80% Pet/20% MC wax | 3926–4822* | 0.31–33* |
| 91% Pet/9% MC Wax | 1983 | 0.15 |
| Petrolatum | 1080–1345 | 0.24 |
| 90% Pet/10% min oil | 767–780 | 0.26 |
| 80% Pet/20% min oil | 354–430 | 0.29–0.34 |
| 60% Pet/40% min oil | 111–115 | 0.42 |
| 40% Pet/60% min oil | 4.8–5.3 | 0.87 |
| Mineral (min) oil | 0.81–0.82 | 1.0 |
| 5% SE†/95% min oil | 1580–1787 | 0.16 |
| 95.9% SBO/4.1% MC wax | 780–890 | 0.13–0.16 |
| 80% Pet/20% Polydecene | 283–292 | 0.32–0.34 |
| 65% Pet/35% Polydecene | 115–120 | 0.4 |
| 20% Pet/80% Polydecene | 0.83 | 0.97–1.0 |
| 20% SE†/80% Polydecene | 1897–2035 | 0.19–0.22 |
| 80% Pet/20% Hydrogenated polybutene | 140–585 | |

*Measured with same instrument, but with 2 cm parallel plate geometry
**Too stiff and solid to obtain readings
†SE solid is a sucrose ester solid and is an example of a preferred polyol fatty acid polyester, SBO is soybean oil and Pet is petrolatum.

Note that mineral oil, microcrystalline wax and some other lipids by themselves have rheological properties that are unsuitable for use in the present liquid compositions; but may be blended with other lipids to provide acceptable lipid blends.

In some cases, the lipid in this present invention can also be defined in terms of its solubility parameter, as defined by Vaughan in Cosmetics and Toiletries. Vol. 103, p47–69, October 1988. A lipid having a Vaughan Solubility Parameter Value (VSP) of from 5 to 10, preferably 5.5 to 9, more preferably where at least 70% of said lipid has a VSP of 6.5 to 7.75 is suitable for use in the liquid compositions herein. The Vaughan Solubility Parameters of some preferred lipid moisturization agents are set forth in the Table below.

VAUGHAN SOLUBILITY PARAMETER TABLE*

| Cyclomethicone | 5.92 |
|---|---|
| Squalene | 6.03 |
| Mineral Oil | 7.09 |
| Petrolatum | 7.33 |
| Isopropyl Palmitate | 7.78 |
| Isopropyl Myristate | 8.02 |
| Castor Oil | 8.90 |
| Cholesterol | 9.55 |

*As reported in Solubility, Effects in Product, Package, Penetration and Preservation, C. D. Vaughan, Cosmetics and Toiletries, Vol. 103, October 1988.

Notwithstanding the rheological and solubility requirements described hereinabove, a wide variety of lipid type materials and mixtures of materials are suitable for use in the compositions of the present invention. Preferably, the lipid is selected from the group consisting of hydrocarbon oils and waxes, silicones, fatty acid derivatives, cholesterol, cholesterol derivatives, di and tri-glycerides, vegetable oils, vegetable oil derivatives, liquid nondigestible oils such as those described in U.S. Pat. Nos. 3,600,186 to Mattson; Issued Aug. 17, 1971 and 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk -tri-glycerides, wax esters, beeswax derivatives, sterols, phospholipids hydroxylated milk glyceride, beeswax, spermaceti, myristyl myristate, stearyl stearate carnauba and candelilla waxes, cholesterol fatty acid esters and homologs thereof, lecithin and derivatives, Sphingo lipids, ceramides, glycosphingo lipids and homologs thereof and mixtures thereof. Fatty acids, fatty acid soaps and water soluble polyols are specifically excluded from our definition of a lipid. Thus stearic acid, glycerine and propylene glycol are excluded from our definition of a lipid.

Hydrocarbon oils and waxes: Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof Nonlimiting examples of silicones useful herein are described in U.S. Pat. No. 5,011,681, to Ciotti et al., issued Apr. 30, 1991, which is incorporated by reference.

Di and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of lipid is composed of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene; dimethicones, alkyl siloxane, polymethylsiloxane, methylphenylpolysiloxane and mixtures thereof When as blend of petrolatum and other lipids is used, the ratio of petrolatum to the other selected lipids (hydrogenated or unhdyrogenated polybutene or polydecene or mineral oil) is preferably from about 10:1 to about 1:2, more preferably from about 5:1 to about 1:1.

The size of the lipid droplets within the emulsion preferably ranges from about 0.1 microns to 100 microns, excluding anomalous very small or a few very large droplets. Preferably greater than 25% of the lipid droplets are from 5 microns to 120 microns and more preferably at least 40% of the lipid droplets are from about 5 microns to 25 microns. An especially preferred droplet size range is from 15% to 35% of droplets having a droplet size of 0.1 to 5 micron, 15 to 45% having a droplet size of between 5 and 10 microns, from 30% to 50% having a droplet size between 10 and 25 micron, and less than 15% having a droplet size greater than 25 microns. It is a surprising aspect that high levels of large droplet size lipid can be stable in a liquid cleansing composition and also deposit efficacious levels in the washing process. While not being bound by theory, larger droplets typically deposit more efficiently than smaller droplets.

C. The Dual Cleansing and Lipid Moisturizing Liquid Oil-in-Water Emulsions

Surprisingly, it has been discovered that the emulsions of the present invention which contain crystalline hydroxyl-containing stabilizers are much more stress stable than emulsions which contain non-hydroxyl containing crystalline waxes such as ethylene glycol distearate or tristearin. Moreover, as hereinbefore discussed, the dual cleansing and moisturizing liquid emulsion compositions of the present invention exhibit good lathering characteristics and are formulated such that an effective amount of lipid is actually deposited on the skin to provide superior moisturization benefits.

The deposition of lipid on the skin can be measured via the following lipid deposition protocol. This protocol is modeled after how skin cleansing products are typically used by consumers. The protocol is an in vivo test using at least 6 subjects. The protocol consists of a product application stage followed by a determination of the deposited lipid amount. The quantification of lipid is in vivo and as such has a wide variance due to differences in skin type and condition. To offset this, a balanced design is used to test prototypes; balanced in skin type and using a large base size.

Preparation For Lipid Deposition Protocol

The subject wets the entire surface of the inner forearm with 95°–100° F. tap water for five seconds. The subject then saturates a puff, such as that described in Campagnoli; U.S. Pat. No. 5,144,744; Issued Sep. 8, 1992, and allows the puff to drain for 10 seconds. One milliliter of product is applied to the forearm of the subject and then the product is rubbed with the puff for 10 seconds to generate lather. The lather is allowed to remain on the forearm for fifteen seconds, followed by a thorough rinse for fifteen seconds with the water flowing from inner elbow to wrist. The subject arm is then pat dried with a paper towel. The subject then allows the arm to "air" dry for 30 seconds.

Lipid Deposition Protocol

Lipid deposition on the skin is measured using a Sebumeter SM810 which is commercially available from Courage and Khazaka GmbH and is reported to be recognized by the scientific world. The Sebumeter measures lipid on the skin via photometry of a special plastic strip, which becomes transparent when it absorbs lipids. The plastic strip is extended over a mirror which is connected to a spring. The measuring head of the device (comprised of spring, mirror and plastic strip) is pressed against the skin for 30 seconds. The value ($\mu$g/sq. cm) is indicative of the amount of lipid on the skin, and increases with increased amount of lipid. The method is insensitive to humidity. Sebumeter readings (3) are taken along the length of the forearm and the Lipid Deposition Value, LDV, ($\mu$g/sq. cm) is defined as the mean of the 3 readings, divided by 0.56 for petrolatum containing lipid mixtures. The 0.56 value is a conversion factor to translate sebumeter readings with petrolatum containing lipids to actual deposition levels in $\mu$g/sq. cm. Lipid deposition values of from 15 to 200 $\mu$g/sq. cm., more preferably from 30 to 150 $\mu$g/sq. cm. are preferred.

The Sebumeter has the following limitations:

1. The Sebumeter tape also detects natural skin lipids. A criterion of this test was that subjects baseline value measured on the Sebumeter, prior to washing, be less than or equal to 3 $\mu$g/sq. cm of forearm skin.

2. The Sebumeter like other surface extraction measurements may not measure all the deposited lipid, if the skin topography is undulating it is possible that deposited lipid may not be extracted by the Sebumeter tape.

3. The Sebumeter tape becomes saturated at a LDV of above about 300 $\mu$g/sq. cm; so this method can be used only for deposition values below about 300 $\mu$g/sq. cm.

4. Different lipid systems will have different conversion factors. For testing non-petrolatum lipids, a new calibration curve is required.

The dual cleansing and moisturizing liquid emulsions of the present invention have a Lipid Deposition Value of at least 5 micrograms per square centimeter. This means that it will deposit at least 5 micrograms of lipid on a square centimeter of forearm skin using the protocol described above.

It is believed that, for certain of the emulsions of the present invention, that the rheological properties of the emulsion can have an important effect on lipid deposition and emulsion stability. In particular, it is believed that for some compositions it is desired to have a high degree of pseudoplasticity (low n and high k value). However, the pseudoplasticity of the emulsion may be of less importance when a puff, such as the polymeric diamond mesh sponge described in Campagnoli; U.S. Pat. No. 5,144,744; Issued Sep. 8, 1992, is used to apply the emulsion to the skin. Preferred n and k values to the emulsions of the present invention are set forth in the Table below:

| Finished Product Rheological Table | | |
| --- | --- | --- |
| Range | k (poise @ (1/sec)$^{n-1}$ | n (dimensionless) |
| More Preferred | 250–500 | 0.20–0.05 |
| Preferred | 175–250 | 0.30–0.20 |
| Less Preferred | 100–175 | 0.40–0.30 |

The Carrimed CSL 100 Controlled Stress Rheometer is used to determine Shear Index, n, and Consistency, k, for the respective liquid cleansing product and lipid herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10−4 rad/sec, then this rate of strain is reported as a shear rate. These data are used to create a viscosity $\mu$ Vs. shear rate $\gamma'$ flow curve for the material. This flow curve can then be modeled in order to provide a mathematical expression that describes the material's behavior within specific limits of shear stress and shear rate. These results were fitted with the following well accepted power law model (see for instance: *Chemical Engineering*, by Coulson and Richardson, Pergamon, 1982 or *Transport Phenomena* by Bird, Stewart and Lightfoot, Wiley, 1960):

$$\text{Viscosity, } \mu = k\,(\gamma')^{n-1}$$

The emulsions of the present invention also have good lathering characteristics. Lather can be measured according to either of the following tests:

Liquid Hand Lather Test

The hand wash lather test is used to provide in-use lather volume measurements for the lather performance of skin cleansing liquids. The test measures the lather volume generated under a soil load and without soil. Synthetic soil is used for the test reported herein. Its formula is reported in U.S. Pat. No. 4,673,525 to Small et al. issued Jun. 16th 1987, incorporated herein by reference.

The technician washes hands first with Ivory bar before starting test. The technician then passes one hand through 95F city water, leaving a little water in palm of hand and dispenses 1.7 mls of test product into that hand. The technician then passes the other hand through the water and spreads product by rubbing palms together. The product is circulated on the palm and fingers of the hand 3 times then over the back of the hands once. This procedure is repeated 5 times.

An additional 2 mls of water is added to the hands and the product is again spread through the hands and circulated as outlined above continuously 5 more times, then the product is gathered/scraped into a 250 ml beaker and measured based on volume usually expressed in milliliters.

Puff Lather Method

Equipment
- 1–800 ml beaker
- 1 —potato utensil (waffle design with circular flat bottom)
- 10 ml syringe timer
- 95° city water
- Olay Body Wash Puff (medium soft, 3 pieces)

Method

1. Fill syringe with 4.5 mls of product.
2. Add 150 mls of 95° city water to beaker.
3. Wet puffin 95° city water for 3 seconds. Squeeze out excess water.
4. Put puff in beaker, string side down.
5. Add product to the puff in a circular motion, covering the surface of the puff (not concentrated in the middle).
6. Wet utensil for 3 seconds.
7. Set timer for 30 seconds. Using the utensil, push the puff down to the 200 ml marker then bring up to the 600 ml marker (this counts as one time). Do this procedure 30 times in 30 seconds (each up and down motion takes 1 second).
8. Take a reading by allowing the utensil to rest on the puff (250 mls) without pressure. Measure the lather height above the utensil. Subtract the water level (approx. 100 mls.).

The dual moisturizing and cleansing liquid of this invention can be made by the following process, which utilizes trihydroxystearin as a representative stabilizer:

Single Vessel Process

1. Trihydroxystearin is added to distilled water and allowed to mix until fully hydrated (appropriate ventilation and dust masks should be worn to prevent inhalation of dust).
2. The surfactants (anionic, amphoteric, cationic and nonionic) are added and the mixture is heated to 190° F. until the trihydroxystearin is fully melted and dissolved (87.8° C.). While heating, the mixture is subjected to shear via a medium to high agitator speed.
3. The trihydroxystearin dispersion is fast cooled utilizing a plate and frame heat exchanger to a temperature of about 110° F. to 80° F. (43° C. to 27° C.) to form trihydroxystearin crystals. The optimum freeze-out temperature for the other wax-like stabilizers is determined from the cooling curve of a DSC spectrum.
4. Tetrasodium EDTA and Glydant are added. Perfume is added. The mixture is continuously stirred at a medium speed.
5. If optional Polymer is to be included, it is added in one of several ways, depending on type. If the polymer is polyquaternium 10 or polyox, it is premixed with glycerin and added as a premix, mixed 5 minutes before continuing. Alternatively, Polyquaternium 10 or polyox is premixed with water and allowed to stir for 10–20 minutes to allow hydration of the polymer.
6. Any additional sensory aids such as silicones are added and allowed to mix 1–2 minutes.
7. The batch is adjusted for water loss by weighing and back adding the amount lost due to evaporation during batch making.
8. A premix of lipid blend, (e.g. polybutene or mineral oil with petrolatum), at a temperature of 105°–110° F. (40°–43° C.), is added to the mixture at a temperature of 105°–110° F. (40°–43° C.) and allowed to stir for 2 minutes at a slow to medium setting. The duration and intensity of the mixing after lipid addition is considered important, especially with regards to particle size. Accordingly, if mixed too long or too fast, particle size and the resultant lipid deposition decreases.

EXAMPLES

The following include some non-limiting examples of the present invention:

EXAMPLE 1–3

Typical Examples of Products Stabilized with Trihydroxystearin:

| Ingredients | #1 | #2 | #3 | #4 |
|---|---|---|---|---|
| Sodium C12/14 Alkyl Ether Glycerol Sulfonate | 11.57 | 0.00 | 6.86 | 12.0 |
| Ammonium Laureth-3 Sulfate | 3.86 | 7.38 | 0.00 | 3.0 |
| Potassium Myristate | 0.00 | 0.00 | 6.86 | 0.0 |
| Myristic Acid | 0.00 | 0.00 | 0.00 | 1.0 |
| Myristic Alcohol | 0.00 | 0.00 | 0.00 | 1.0 |
| Ammonium Lauryl Sulfate | 0.00 | 4.92 | 0.00 | 0.0 |
| Cocamidopropyl Betaine | 2.57 | 3.69 | 2.29 | 3.0 |
| Trihydroxystearin (Thixcin R) (Stabilizer) | 1.75 | 2.00 | 1.75 | 1.75 |
| Petrolatum | 11.60 | 11.60 | 11.60 | 0.0 |
| Liquid Cottonseed SPE | 0.00 | 0.00 | 0.00 | 15.3 |
| Solid $C_{22}$ SPE | 0.00 | 0.00 | 0.00 | 1.20 |
| Hydrogenated Polyisobutene | 2.90 | 2.90 | 2.90 | |
| Glycerin | 6.24 | 6.24 | 6.24 | |
| Tetrasodium EDTA | 0.13 | 0.13 | 0.13 | 0.13 |
| DMDM Hydantoin | 0.14 | 0.14 | 0.14 | |
| Perfume | 0.80 | 0.80 | 0.80 | 0.50 |
| Polyquat-10 (JR-30M) | 0.00 | 0.00 | 0.30 | 0.30 |
| Glydant | 0.00 | 0.00 | 0.00 | 0.20 |
| Maleated Soybean Oil | 0.00 | 0.00 | 0.00 | 1.0 |
| Water | 59.04 | 60.19 | 60.24 | qs |
| Volume Lather (ml) | 90 | 85 | 90 | — |
| Consistency, k (Poise) | 310 | 355 | 176 | — |
| Shear Index, n | 0.17 | 0.10 | 0.29 | — |
| Shelf Stable | Yes | Yes | Yes | Yes |
| Stress Stable | Yes | Yes | Yes | Yes |

The above examples are shelf stable, stress stable, have good lipid deposition and good lather. Lather is measured according to the Liquid hand Lather Test set forth herein.

Comparative Examples 5–7

The following Comparative Examples 5–7 comprise non-hydroxy waxes as stabilizers. They are included to demonstrate the novelty and advantages of the said crystalline hydroxy wax stabilizers of this present invention.

| Ingredients | #5 | #6 | #7 |
|---|---|---|---|
| Sodium C12/14 Alkyl Ether Glycerol Sulfonate | 11.57 | 4.27 | 6.10 |
| Ammonium Laureate-3 Sulfate | 3.86 | 0.0 | 0.0 |
| Sodium Lauroyl Sarcosinate | 0.0 | 0.0 | 2.0 |
| TEA Lauroyl Sarcosinite | 0.0 | 2.76 | 0.0 |
| Potassium Myristate | 0.0 | 4.35 | 6.30 |
| Cocamidopropyl Betaine | 2.57 | 0.0 | 0.0 |
| Myristic Acid | 0.0 | 0.50 | 0.30 |
| Coco Betaine | 0.0 | 1.97 | 3.20 |
| Tristearin (Stabilizer) | 2.0 | 0.0 | 0.0 |
| Ethylene Glycol Distearate (Stabilizer) | 0.0 | 7.50 | 4.15 |
| Propylene Glycol (MW 400,000) | 0.0 | 0.05 | 0.0 |
| Carbopol 980 (Stabilizer) | 0.0 | 0.0 | 0.50 |
| Polyquat-10 (JR30M) | 0.0 | 0.0 | 0.30 |
| Petrolatum | 11.6 | 11.6 | 13.2 |
| Hydrogenated Polyisobutene | 2.9 | 0.0 | 2.9 |
| Mineral Oil | 0.0 | 2.9 | 0.0 |
| Myristyl Alcohol | 0.0 | 0.0 | 1.0 |
| Glycerin | 6.24 | 6.24 | 6.24 |
| DMDM Hydantoin | 0.14 | 0.0 | 0.37 |
| Tetrasodium EDTA | 0.13 | 0 | 2.00 |
| Perfume | 0.8 | 0.50 | 0.80 |
| Water | 59.04 | 57.36 | 52.94 |
| k (Poise) | 60 | 30 | 141 |

-continued

| Ingredients | #5 | #6 | #7 |
|---|---|---|---|
| n | 0.33 | 0.26 | 0.40 |
| Shelf Stable | Yes | Yes | Yes |
| Stress Stable | No | No | Yes |

The above Comparative Examples are included to demonstrate the advantages of the emulsions of the present invention with respect to stability. Comparative Examples 5 through 7 are lipid containing moisturizing liquid cleansing products which utilize as stabilizers two different non-hydroxy waxes and a non-hydroxy wax-polymer combination, respectively.

Comparative Example 5 utilizes tristearin as a stabilizer in exactly the same matrix and level as was utilized with trihydroxystearin in Example 1 above. This comparison is important in that these two molecules are identical with the exception of 3 hydroxyl groups on trihydroxystearin. Correspondingly, the tristearin prototype exhibits a much lower consistency and fails to be stress stable. This is in marked contrast to Example 1 with trihydroxystearin which exhibits much greater consistency and stress stability. This comparison clearly confirms the importance of the hydroxyl groups in achieving a highly pseudoplastic and stress stable liquid cleansing product utilizing crystalline waxes as stabilizers/thickeners.

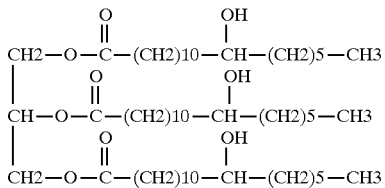

Trihydroxystearin

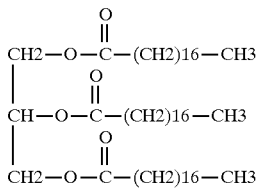

Tristearin

Example 6 is a moisturizing lipid containing liquid cleanser which utilizes ethylene glycol distearate as a stabilizer. Ethylene glycol distearate is a non-hydroxy wax and like tristearin above, this stabilizer also imparts a rather low consistency and a lack of stress stability to the liquid cleanser.

Example 7 demonstrates that utilizing a stabilizing polymer with ethylene glycol distearate can improve the stress stability. However, the addition of the polymer increases the shear index, n, of the cleanser. The only crystalline waxes that were found to be capable of providing sufficient stress stability without necessitating a polymer were the waxes containing hydroxyl groups such as those described herein. The above information further supports the notion that the presence of hydroxyl groups on crystalline waxes are key to this invention.

Examples 8 through 11 are some further non-limiting examples of the present invention.

|  | Example 8 | Example 9 | Example 10 | Example |
|---|---|---|---|---|
| Ammonium Laureth-3 sulfate | 9.45 | 9.45 | 9.45 | 9.45 |
| Ammonium Lauryl sulfate | 3.15 | 3.15 | 3.15 | 3.15 |
| Na Lauroamphoacetate | 5.40 | 5.40 | 5.40 | 5.40 |
| Trihydroxystearin | 4.0 | 4.0 | 4.0 | 2.0 |
| Polyquaternium-10 | 0.3 | 0.3 | 0.3 | 0.3 |
| Glycerin | 3.0 | 3.0 | 3.0 | 3.0 |
| Perfume | 0.8 | 0.8 | 0.8 | 0.8 |
| Tetrasodium EDTA | 0.13 | 0.13 | 0.13 | 0.13 |
| Citric Acid | 0.76 | 0.76 | 0.76 | 0.76 |
| Petrolatum | 16.50 | 11.20 | 16.50 | — |
| Polybutene (H1900) | 0.0 | 4.80 | 0.0 | — |
| Lauryl Alcohol PEG14M | — | — | 1.0 | 2.0 |
| Fumed Silica | 0.0 | 0.0 | 0.1 | 1.5 |
| Cottonseed Sucrose Octaester | — | — | — | 15.3 |
| Sucrose octaesters from $C_{22}$ Fatty Acids | — | — | — | 1.2 |
| Water | Q.S. | Q.S. | Q.S. | Q.S. |
| Lather Volume (ml) | 400 | — | 400 | — |
| Lipid Deposition* | 21.4 | 33.9 | 23.2 | — |
| Stress Stable | Yes | Yes | Yes | — |

*The 0.56 Conversion factor for petrolatum is used here as an approximation. The Lather volume reported in this table is measured according to the Puff Lather Method set forth hereinbefore.

What is claimed is:

1. A stress stable, rinse-off, lathering skin cleansing liquid composition comprising by weight parts of the liquid composition:
   (a) from about 0.5 parts to 10 parts of a crystalline trihydroxystearin
   (b) from about 1 part to about 30 parts of lipid skin moisturizing agent having a shear index at 35° C. in the range 0.1 to 0.9 and a consistency k at 35° C. in the range 5 to 5,000 poise;
   (c) from about 5 part to about 30 parts of surfactant having a combined critical micelle concentration equilibrium surface tension value of from 15 to 50 dynes/cm; and
   (d) water;
wherein said stress stable, rinse-off lathering skin cleansing liquid composition has a Lipid Deposition Value (LDV) of from about 5 to about 1000 μg/sq. cm and wherein said stress stable, rinse-off lathering skin cleansing liquid composition is stable for at least 2 weeks at 38° C.

2. The stress stable rinse-off lathering skin cleansing liquid composition of claim 1 wherein said stress stable, rinse-off lathering skin cleansing liquid composition has a shear index at 35° C. in the range 0.30–0.05 and a consistency k at 35° C. in the range 175–500 poise.

3. The stress stable rinse-off lathering skin cleansing liquid composition of claim 1 which comprises (a) from about 0.75 to about 8 parts crystalline, trihydroxystearin, (b) from about 5 to about 30 parts lipid skin moisturizing agent, wherein said lipid skin moisturizing agent has a viscosity consistency k value of 10 poise to 3,000 poise at 35° C. and a shear index at 35° C. in the range 0.1 to 0.5; (c) from about 5 to about 25 parts of a surfactant having a combined critical micelle concentration equilibrium surface tension value of from 25 to 40 dynes per cm at 25° C.; and (d) from about 30 parts to about 80 parts water; wherein said liquid composition has a Lipid Deposition Value of 15 to 200 μg/sq. cm.

4. The stress stable, rinse-off lathering skin cleansing liquid composition of claim 3 wherein said lipid skin moisturizing agent is selected from the group consisting of: hydrocarbon oils and waxes, silicones, fatty acid derivatives, cholesterol, cholesterol derivatives, di- and tri-glycerides, vegetable oils, vegetable oil derivatives, liquid nondigestible oils, blends of liquid digestible or nondigestible oils with solid polyol polyesters, acetoglyceride esters, alkyl esters, alkenyl esters, lanolin and lanolin derivatives, milk triglycerides, wax esters, beeswax derivatives, sterols, phospholipids and mixtures thereof.

5. The stress stable, rinse-off lathering skin cleansing liquid composition of claim 4 which comprises from about 1.25 to about 5 parts of the crystalline trihydroxystearin.

6. The stress stable rinse-off lathering skin cleansing liquid composition of claim 3 wherein said lipid skin moisturizing agent is selected from the group consisting of: petrolatum, mineral oil, micro-crystalline waxes, polyalkenes, paraffin, cerasin, ozokerite, polyethylene, perhydrosqualene, dimethicones, cyclomethicones, alkyl siloxanes, polymethylsiloxanes, methylphenylpolysiloxanes, hydroxylated milk glyceride, castor oil, soy bean oil, maleated soy bean oil, safflower oil, cotton seed oil, corn oil, walnut oil, peanut oil, olive oil, cod liver oil, almond oil, avocado oil, palm oil, sesame oil, liquid sucrose octaesters, blends of liquid sucrose octaesters and solid polyol polyesters, lanolin oil, lanolin wax, lanolin alcohol, lanolin fatty acid, isopropyl lanolate, acetylated lanolin, acetylated lanolin alcohols, lanolin alcohol linoleate, lanolin alcohol riconoleate, beeswax, beeswax derivatives, spermaceti, myristyl myristate, stearyl stearate, carnauba and candelilla waxes, cholesterol, cholesterol fatty acid esters and homologs thereof, lecithin and derivatives, Sphingo lipids, ceramides, glycosphingo lipids and homologs thereof, and mixtures thereof.

7. The stress stable rinse-off lathering skin cleansing liquid composition of claim 6, wherein said stress stable, rinse-off lathering skin cleansing liquid composition has a Lipid Deposition Value in the range 30 to 150 μg/sq.cm; and wherein at least 75% of said lipid skin moisturizing agent is selected from the group consisting of: petrolatum, blends of petrolatum and high molecular weight polybutene, mineral oil, liquid sucrose octaesters, blends of liquid sucrose octaesters and solid polyol polyesters, hydrogenated or nonhydrogenated polybutene, micro-crystalline wax, polyalkene, paraffin, cerasin, ozokerite, polyethylene, perhydrosqualene; dimethicones, alkyl siloxane, polymethylsiloxane, methylphenylpolysiloxane and mixtures thereof.

8. The stress stable rinse-off lathering skin cleansing composition of claim 7 wherein the lipid skin moisturizing agent comprises a blend of petrolatum and polybutene in a ratio of from about 5:1 to about 1:1.

9. The stress stable rinse-off lathering skin cleansing composition of claim 7 wherein the lipid skin moisturizing agent comprises blends of liquid sucrose octaesters and solid polyol polyesters in a ratio of from about 96:4 to about 80:20.

10. The stress stable, rinse-off lathering skin cleansing liquid composition of claim 7 which comprises from about 10 parts to about 25 parts of lipid skin moisturizing agent; and wherein said lipid skin moisturizing agent has a consistency k value of 50 to 2000 poise, a shear index of from 0.20 to about 0.50.

11. The stress stable, rinse-off lathering skin cleansing liquid composition of claim 1 which comprises from about 5 to about 25 parts surfactant, and wherein said surfactant is selected from the group consisting of acyl isethionates, acyl sarcosinates, alkylglycerylether sulfonates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphates, alkyl ether sulfates and mixtures thereof, wherein said surfactants contain $C_8$ to $C_{22}$ alkyl chains and wherein the counterion is selected from the group consisting of: Na, K, $NH_4$, and $N(CH_2CH_2OH)_3$.

12. The stress stable, rinse-off lathering skin cleansing liquid composition of claim 1 which contains additionally from 0.1 to about 1 part of a water-dispersible, gel-forming polymer.

13. The stress stable, rinse-off lathering skin cleansing liquid composition of claim 12 wherein the polymer is selected from the group consisting of cationic polysaccharides of the cationic guar gum class with molecular weights of 1,000 to 3,000,000; anionic, cationic and nonionic homopolymers derived from acrylic or methacrylic acid; anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines; polyethylene glycol of molecular weight from 100,000 to 4,000,000; and mixtures thereof.

14. The stress stable, rinse-off lathering skin cleansing liquid composition of claim 1 wherein said stress stable, rinse-off lathering skin cleansing liquid composition additionally comprises from about 0.5 to about 25 parts water soluble, organic material and wherein said water soluble organic material is selected from the group consisting of alkane diols; guanidine; glycolic acid and glycolate salts; lactic acid and lactate salts; polyhydroxy alcohols; polyethylene glycol; sugars and starches; sugar and starch derivatives; panthenol; pyrrolidone carboxylic acid; hyaluronic acid; lactamide monoethanolamine; acetamide monoethanolamine; urea; and ethanol amines of the general structure $(HOCH_2CH_2)_xNH_y$ where x=1–3; y=0–2, and x+y=3, and mixtures thereof; and wherein said water soluble organic material is at least 50% soluble in water.

15. The stress stable, rinse off lathering skin cleansing liquid composition of claim 1 which additionally comprises from about 0.5 parts to about 5 parts fumed silica.

16. The stress stable, rinse-off lathering skin cleansing liquid composition of claim 1 which additionally comprises from about 0.5 to about 3 parts of maleated soybean oil.

17. A personal bath or body cleansing kit comprising:
a) a light weight polymeric diamond mesh personal cleansing hand-held sponge; and
b) the stress stable, rinse-off lathering skin cleansing liquid composition of claim 1.

18. A stress stable, rinse-off lathering skin cleansing liquid composition comprising by weight parts of the liquid composition:
(a) from about 1.25 parts to 5 parts of a water insoluble crystalline trihydroxystearin;
(b) from about 10 parts to about 25 parts of lipid skin moisturizing agent having a shear index at 35° C. in the range 0.2 to 0.5 and a consistency k at 35° C. in the range 50 to 2,000 poise;
(c) from about 10 parts to about 25 parts of surfactant having a combined critical micelle concentration equilibrium surface tension value of from 15 to 50 dynes/cm;
(d) from about 40 to about 65 parts water;
wherein said stress stable, rinse-off lathering skin cleansing liquid composition has a Lipid Deposition Value (LDV) of from about 30 to about 150 $\mu g/sq.cm$.

19. The stress stable, rinse-off lathering skin cleansing liquid composition of claim 18 wherein said stress stable lathering skin cleansing liquid composition has a shear index at 35° C. in the range 0.30–0.05 and a consistency k at 35° C. in the range 175–500 poise.

* * * * *